United States Patent [19]

Valcavi et al.

[11] Patent Number: 4,625,021

[45] Date of Patent: Nov. 25, 1986

[54] HIGH YIELD PROCESS FOR PREPARING BETA-LACTAM ANTIBIOTICS HAVING A HIGH PURITY DEGREE

[75] Inventors: Umberto Valcavi; Paolo Farina; Vittorio Marotta, all of Milan, Italy

[73] Assignee: Istituto Biochimico Italiano Giovanni Lorenzini S.p.A., Italy

[21] Appl. No.: 740,251

[22] Filed: Jun. 3, 1985

[30] Foreign Application Priority Data

Jul. 30, 1984 [IT] Italy .............................. 22122 A/84

[51] Int. Cl.$^4$ ................. C07D 501/04; C07D 501/06; C07D 499/12
[52] U.S. Cl. .................................... 540/230; 540/215; 540/317
[58] Field of Search ................. 260/239.1; 544/30, 16, 544/17, 21, 22, 23, 24, 25, 26, 27, 28, 29

[56] References Cited

U.S. PATENT DOCUMENTS 3,963,704 6/1976 Ferres .............................. 260/239.1

Primary Examiner—Natalie Trousof
Assistant Examiner—Vera C. Clarke
Attorney, Agent, or Firm—Ostrolenk, Faber, Gerb & Soffen

[57] ABSTRACT

A high yield process for preparing beta-lactam antibiotics having a high purity degree, in particular derivatives of the cephalosporanic and penicillanic acids, of the formula:

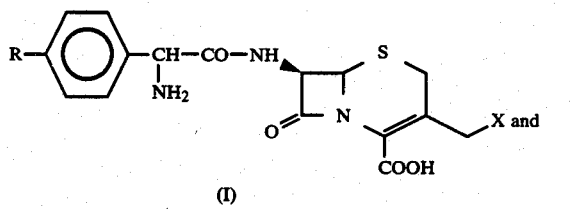

(I)

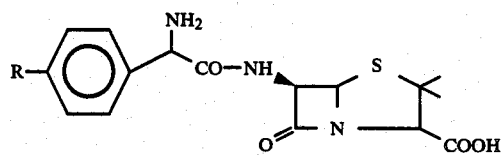

(II)

by condensation of the compounds

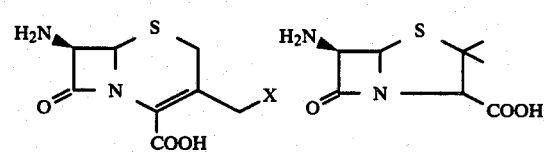

(III) and (IV)

where X=H —OCH$_3$
(suitably blocked), with a chloride of the formula

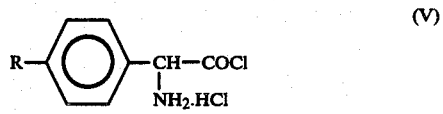

(V)

wherein R=H, OH
in which said condensation is carried out in the presence of a nicotinic or isonicotinic base.

5 Claims, No Drawings

HIGH YIELD PROCESS FOR PREPARING BETA-LACTAM ANTIBIOTICS HAVING A HIGH PURITY DEGREE

DESCRIPTION OF THE INVENTION

The invention relates to the high yield production of beta-lactam antibiotics having a high purity degree, in particular, of derivatives of the cephalosporanic and penicillanic acids of the formula:

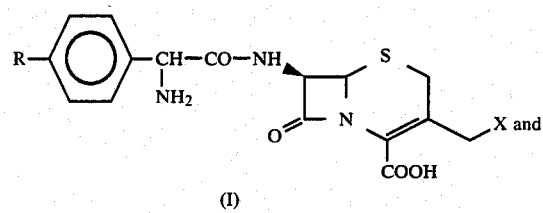
(I)

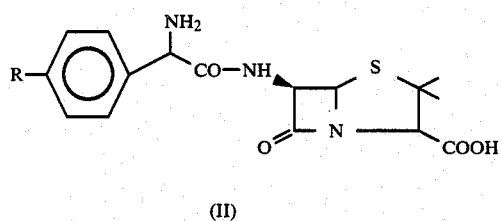
(II)

by silylation of the compounds

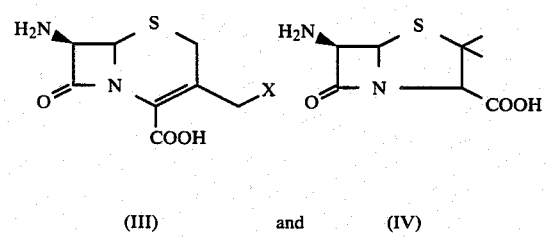
(III) and (IV)

where X=H, —OCH$_3$
with usual silylating agents such as trimethyl-chlorosilane, hexamethyldisilazane, dimethyldichlorosilane and the like, followed by acylation with chlorides of D-α-amino acids, wherein the amine group is blocked as a hydrochloride, of of the general formula

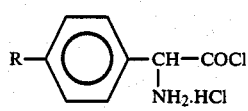
(V)

where R=H, OH
in the presence of HCl acceptors of the general formula

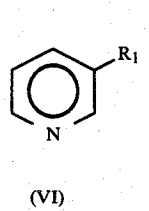
(VI)         (VII)

where

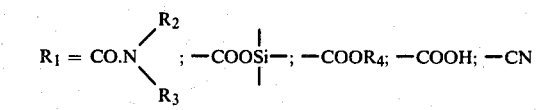

in which
R$_2$=R$_3$=H
R$_2$=H
R$_3$= straight or branched C$_1$-C$_5$ chain alkyl
R$_2$=R$_3$= straight or branched C$_1$-C$_5$ chain alkyl
R$_2$≠R$_3$=straight or branched C$_1$-C$_5$ chain alkyl
R$_4$= straight or branched C$_1$-C$_5$ chain alkyl For example, the silylation reaction may be carried out either with hexamethyldisilazane in methylene chloride or with trimethylchlorosilane in the presence of a base such as triethylamine or diethylamine at a temperature of 0° C. to 42° C.

The reaction of acylation of the previously silylated compound (III) and (IV) is carried out according to per se known methods, by employing the compounds of formula (V), however in the presence of such bases as (VI) or (VII).

These bases have the advantage of showing very low toxicity as regards to the ones usually employed for said reactions, such as pyridine and dimethylaniline.

Bases (VI) and (VII) have, further, the advantage of being soluble in water as well as in the organic solvents, and, therefore, they can be easily eliminated.

The acylation reaction can be effected at a temperature from −40° C. to +40° C.

By operating according to the process of the present invention, recovery of the products which are to be prepared can easily be effected either by extracting and precipitating the zwiterion of isoelectric pH, or by precipitating the hydrochloride by addition of alcohols such as methanol, ethanol, isopropanol, n-propanol and butanol to the reaction mixtures.

The hydrochloride may then be converted to the zwitterion by treating with a suitable base an aqueous solution of the above said product till the isoelectric point.

The process of this invention will now be illustrated by the following examples, limitedly to particular cephalosporins and penicillins; however, one skilled in the art could, without any difficulty, use this procedure for the preparation of further beta-lactam antibiotics, without there by exceeding the scope of the present invention.

EXAMPLE 1

6-(D-α-aminophenyl-acetamido)-2,2-dimethyl-penam-3-carboxylic acid.

To a suspension of (6-APA) 6-aminopenicillanic acid (54 g; 0.25 mole) in methylene chloride (450 ml), diethylamine (36.5; 0.5 mole) is added. To the so obtained solution, at a temperature from 0° to +5° C., trimethylchlorosilane (54.5 g;0.5 mole) is added.

After 90 minutes at 25°-30° C., the silylating reaction is completed.

The reaction mixture is cooled to −30° C. and nicotinamide (36.6 g; 0.3 mole) and D-α-phenylglycine chloride hydrochloride (51.5 g; 0.25 mole) are added.

The suspension is kept two hours at −5° C. and, thereafter, 30 minutes at +10° C.

It is treated with water (300 ml) and the phases are separated.

The aqueous phase is treated with concentrated $NH_4OH$ to the isoelectric point (pH=4.5). After 1 hour at 0°/+5° C., the antibiotic is filtered off and then it is washed with $H_2O$ until disappearance of $Cl^-$.

It is dried under vacuum, to obtain 85 g of ampicillin. $3H_2O$.

Yield: 84.3%
$H_2O$=13.4% (Karl Fisher)
$[\alpha]_d^{20}$=+297°
Mercurimetric titre=850 µg/mg
Acidimetric titre=860 µg/mg
Acidimetric titre=98.2%
Amine titre=97.69%

EXAMPLE 2

6-(D-α- amino-p.HO-phenylacetamido)-2,2-dimethyl-penam-3 carboxylic acid.

At the conditions of Example 1, by utilizing D-α-p.HO-phenylglycine chloride hydrochloride, amoxicillin 3 $H_2O$ (84.5 g) is obtained.

Yield: 80.66%
$H_2O$=13.5% (Karl Fisher)
$[\alpha]_d^{20}$=+301.2°
Microbiologic titre=870 µg/mg
Mercurimetric titre=868 µg/mg
Acidimetric titre=97.6%
Amine titre=99.9%

EXAMPLE 3

7-(D-α-aminophenyl-acetamido)-3-methyl-3-cephem-4-carboxylic acid (7-ADCA)

At the conditions of Example 1, by employing equimolecular amounts of 7-ADCA instead of 6-APA, cephalexin. $H_2O$ (69 g) is obtained.

Yield : 77.5%
$H_2O$=6.6% (Karl Fisher)
$[\alpha]_d^{20}$=+153°
Microbiologic titre=930 µg/mg
Spectrophotometric titre=920 µg/mg
Acidimetric titre=98.7%
Amine titre=97.9%

EXAMPLE 4

7-[D-α-amino-(p.HO-phenyl)-acetamido]-3-methyl-3-cephem-4-carboxylic acid.

At the conditions of Example 3, by employing p.HO-phenylglycine chloride hydrochloride, cefadroxil. $H_2O$ (73.8 g) is obtained.

Yield: 77.5%
$H_2O$=5.6 (Karl Fisher)
Microbiologic titre=930 µg/mg
Spectrophotometric titre=933 µg/mg
Acidimetric titre=99.1%
Amine titre=97.7%

EXAMPLE 5

6-(D-α-aminophenyl-acetamido)-2,2-dimethyl-penam-3-carboxylic acid.

To a suspension of 6-APA (54 g; 0.25 mole) and nicotinic acid (30.75 g; 0.25 mole), $Et_3N$ (75.9 g; 0.75 mole) is added.

To the so obtained solution, at a temperature from 0° to +5° C., trimethylchlorosilane (81.75 g; 0.75 mole) is added. After 90 minutes at 25°-30° C., the reaction mixture is cooled to −30° C. and thereafter D-α-phenylglycine chloride hydrochloride (51.5 g; 0.25 mole) is added.

The suspension is kept two hours at −5° C. and then one further hour at +10° C.

It is treated with water (300 ml) and the phases are separated. The aqueous phase is treated with concentrated $NH_4OH$ to achieve the isoelectric point (pH=4.5).

The product as precipitated is filtered off and then it is washed with water.

It is dried under vacuum to obtain 78 g of ampicillin. $3H_2O$.

Yield: 77.4%
$H_2O$=14.78% (Karl Fisher)
$[\alpha]_d^{20}$=+291°
Microbiologic titre=840 µg/mg
Mercurimetric titre=830 µg/mg
Acidimetric titre=96.8%
Amine titre=96.0%

EXAMPLE 6

7-(D-α-aminophenyl-acetamido)-3-methyl-3-cephem-4 carboxylic acid.

At the same conditions as in Example 5, by utilizing (7-ADCA) 7-aminodeacetoxycephalosporanic acid instead of 6-APA cephalexin $H_2O$ (67 g) is obtained.

Yield: 73.4%
$H_2O$=7.5% (Karl Fisher)
$[\alpha]_d^{20}$=+151°
Microbiologic titre=905 µg/mg
Spectrophotometric titre=900 µg/mg
Acidimetric titre=97.8%
Amine titre=96.9%

EXAMPLE 7

7α-aminophenyl-acetamido)-3-methyl-3-cephem-4-carboxylic acid.

To a suspension of 7-ADCA (53.5 g; 0.25 mole) in methylene chloride (450 ml) $Et_2NH$ (36.5 g; 0.5 mole) is added.

To the so obtained solution, at a temperature of 0° to +5° C., trimethylchlorosilane (54.5 g; 0.5 mole) is added.

After 90 minutes at −35° C., the reaction mixture is cooled to −30° C. and methyl isonicotinate (34.5 g; 0.25 mole) and D-α- phenylglycine chloride hydrochloride (51.5 g; 0.25 mole) are added.

One proceedes as in Example 5 and cephalexin. $H_2O$ (77 g) is obtained.

Yield: 84.3%
$H_2O$=7.5% (Karl Fisher)
$[\alpha]_d^{20}$=+154°
Microbiologic titre=920 µg/mg
Spectrophotometric titre=920 µg/mg
Acidimetric titre=99%
Amine titre=98.2%

EXAMPLE 8

7-(D-α-aminophenyl-acetamido)-3-methyl-3-cephem-4-carboxylic acid.

At the same conditions as Example 7, by employing methyl nicotinate instead of methyl isonicotinate, cephalexin.$H_2O$ (78 g.) is obtained.

Yield=85%
$H_2O$=7.4% (Karl Fisher)
$[\alpha]_d^{20}$=+155°
Microbiologic titre=920 µg/mg
Spectrophotometric titre=915 µg/mg Acidimetric titre=99.2%
Amine titre=98.5%

We claim:

1. A high yield process for preparing penicillin as cepholosporin beta-lactam antibiotics having a high purity degree, characterized in that the acylation of the beta-lactam intermediate is carried out in the presence of a nicotinic or isonicotinic base.

2. A high yield process for preparing derivatives of the cephaloosporanic and penicillanic acids having a high purity degree, of the formula

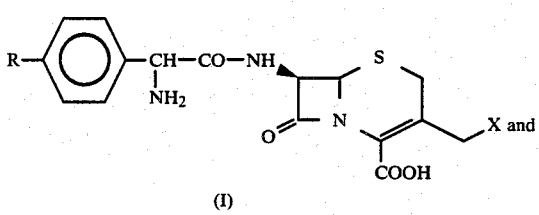

(I)

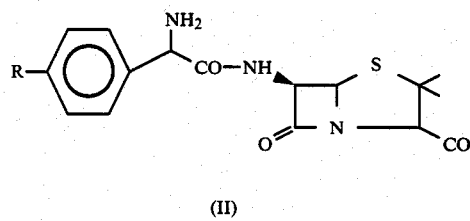

(II)

by silylation of the compounds

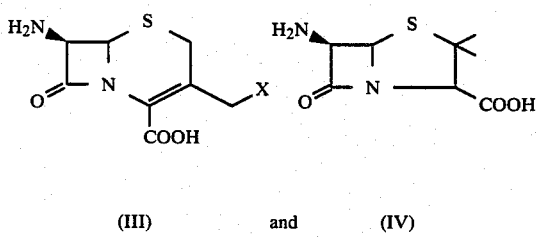

(III)    and    (IV)

where X=H, —OCH₃ followed by acylation with a chloride of the formula:

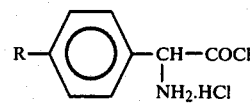

(V)

where R=H, OH
characterized in that said acylation is carried out in the presence of a nicotinic or isonicotinic base.

3. The process according to claim 1 or 2, characterized in that the acylation reaction is carried out in the presence of a compound of the formula:

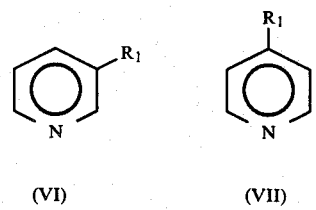

(VI)        (VII)

where $R_1 = CO.N\begin{smallmatrix}R_2\\R_3\end{smallmatrix}$ ; —COOSi—; —COOR₄; —COOH; —CN in which
$R_2=R_3=H$
$R_2=H$
$R_3=$ straight or branched $C_1-C_5$ chain alkyl
$R_2=R_3=$ straight or branched $C_1-C_5$ chain alkyl
$R_2\neq R_3=$ straight or branched $C_1-C_5$ chain alkyl
$R_4=$ straight or branched $C_1-C_5$ chain alkyl 4. The process according to claim 1, characterized in that the said beta-lactam antibiotics are selected from the group consisting of amoxicillin trihydrate, ampicillin trihydrate, cephalexin monohydrate, cefadroxil monohydrate, cephaloglycin and p-hydroxycephaloglycin.

5. The process according to claim 3 characterized in that the chloride is D-alpha-phenylglycine chloride hydrochloride or D-alpha-pHO-phenylglycine chloride hydrochloride and the base is nicotinamide, methyl nicotinate or methyl isonicotinate.

* * * * *